United States Patent [19]
Holub et al.

[11] Patent Number: 5,705,727
[45] Date of Patent: Jan. 6, 1998

[54] BF$_3$ RECOVERY PROCESS

[75] Inventors: Richard A. Holub; Scott D. Soltis, both of Houston; Cynthia W. Hermann, Pearland, all of Tex.

[73] Assignee: Amoco Corporation, Chicago, Ill.

[21] Appl. No.: 489,975

[22] Filed: Jun. 13, 1995

[51] Int. Cl.$^6$ .................. C07C 2/02; C07C 7/00
[52] U.S. Cl. ................. 585/525; 585/800; 585/904
[58] Field of Search ................ 585/525; 423/293

[56] References Cited

U.S. PATENT DOCUMENTS

| | | | |
|---|---|---|---|
| 4,032,591 | 6/1977 | Cupples et al. | 260/683.65 |
| 4,263,467 | 4/1981 | Madgavkar et al. | 585/525 |
| 4,409,415 | 10/1983 | Morganson et al. | 585/525 |
| 4,956,512 | 9/1990 | Nissfolk et al. | 585/521 |
| 4,981,578 | 1/1991 | Tycer et al. | 208/262.1 |
| 5,180,403 | 1/1993 | Kogure | 55/53 |
| 5,254,784 | 10/1993 | Nurminen et al. | 585/525 |

OTHER PUBLICATIONS

EP A 0 364889 (Idemitsu Petrochemical) 15 Apr. 1990.
EP A 0 594 065 (Idemitsu Petrochemical) 27 Apr. 1994.
EP A 0318 186 (Neste Oy) 31 May 1989.

*Primary Examiner*—Glenn A. Caldarola
*Assistant Examiner*—In Suk Bullock
*Attorney, Agent, or Firm*—James R. Henes; Stephen L. Hensley

[57] ABSTRACT

A process for the recovery of BF$_3$ from crude oligomerization reaction product mixture containing dissolved BF$_3$ is described, the process being characterized by vaporization of BF$_3$ from the crude oligomerization reaction product mixture in a vaporization zone at a temperature insufficient to decompose BF$_3$ or any BF$_3$ promoter-complex in the mixture. BF$_3$ from the vaporization zone is then contacted with a liquid olefin composition under conditions to absorb BF$_3$, in an absorption zone, forming a mixture comprising liquid olefin composition and BF$_3$. The liquid olefin composition may be utilized directly for oligomerization of the liquid olefin therein.

5 Claims, 1 Drawing Sheet

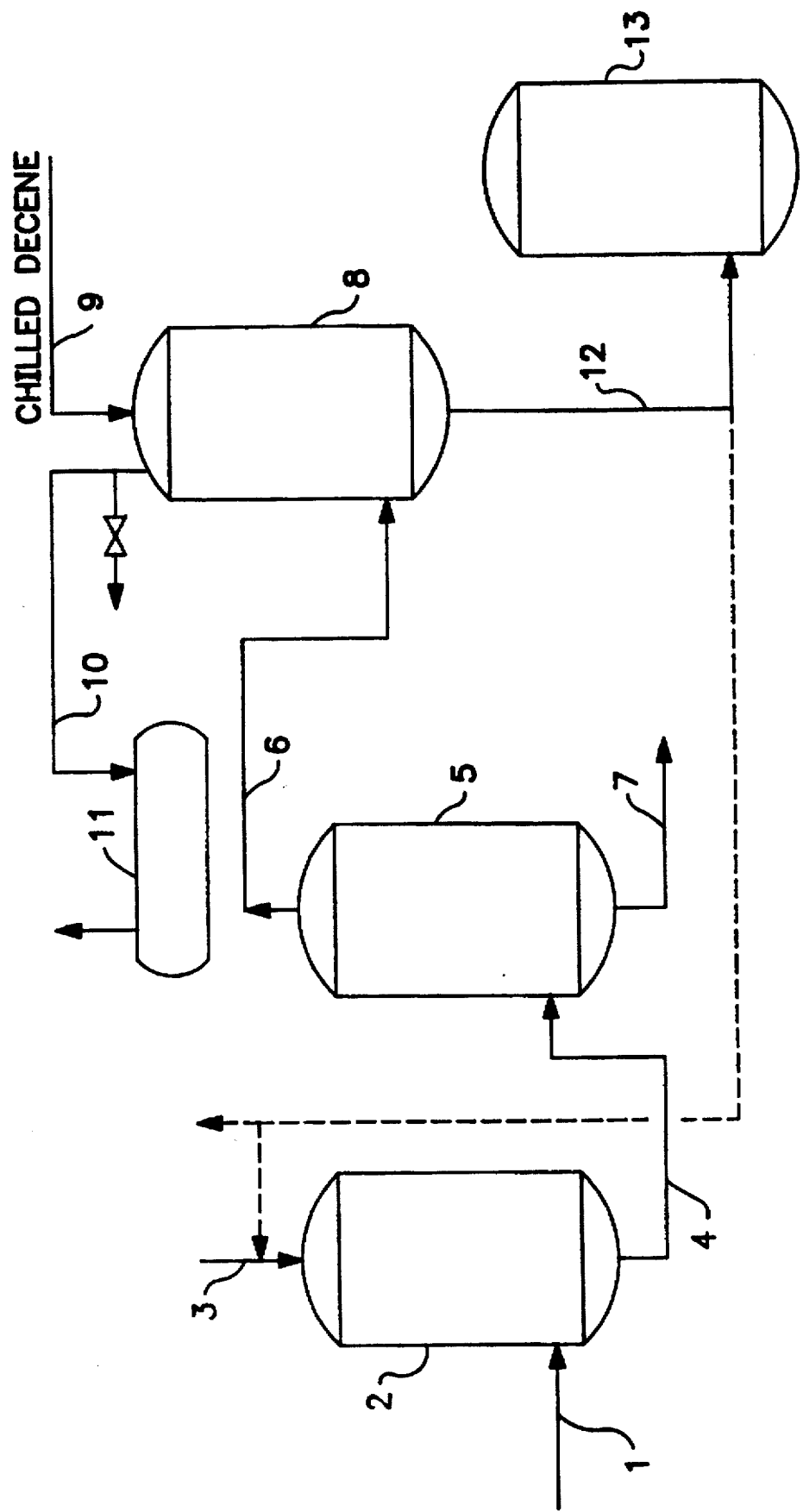

BF₃ RECOVERY PROCESS

FIELD OF THE INVENTION

The invention relates to the improved utilization or recovery of boron trifluoride ($BF_3$) in a process for the oligomerization of an olefin or olefin-containing mixture wherein $BF_3$ is employed as a catalyst or catalyst component. In particular, the invention concerns the recovery of boron trifluoride ($BF_3$) from crude reaction product mixture derived from the oligomerization of an olefin or olefin-containing mixture.

BACKGROUND OF THE INVENTION

The production of oligomers from olefin or olefin-containing mixtures, particularly from alpha olefins, is well known, as is the use of the oligomerization product or products in a variety of lubricants and functional fluids. In preferred processes for the oligomerization of olefins, boron trifluoride is employed as a catalyst for the oligomerization reaction. However, because $BF_3$ is a relatively slow catalyst, a "promoter" or co-catalyst composition, which may be selected from a wide variety of materials, is commonly employed with the $BF_3$ to improve reaction rates.

In at least one process utilizing $BF_3$ and a promoter, the promoter composition, e.g., an oxygenated organic material, such as an alkanol, is believed to form a stable complex or adduct with $BF_3$ supplied to the reaction zone. Preferably, the $BF_3$ is supplied to the reaction zone in an excess of that required for formation of the complex. In the case of such oxygen-containing promoter, for example, the $BF_3$ is commonly supplied in a ratio of from about 1.0 moles to about 4.0 moles of $BF_3$ per mole of oxygen atoms in the compound, although there is no actual limit. The excess $BF_3$ is believed to be loosely associated with the complex, or may simply be dissolved in the reaction mixture, and is susceptible to the recovery procedure of the invention.

Prior to the invention, in at least one olefin oligomerization process utilizing $BF_3$ and promoter, the $BF_3$ catalyst remaining in the oligomerization reaction product mixture, upon recovery of the mixture, has represented a significant cost/disposal problem. That is, $BF_3$ recovery in a reusable form from the reaction product mixture has been difficult because of the unusual properties of $BF_3$ and the nature of oligomerization chemistry. As a result, rather than attempt recovery of the $BF_3$, the catalyst has been treated in a variety of ways, such as by reaction thereof with an ammonium or alkali metal compound, followed by appropriate disposal of the reaction product. However, increasing environmental consciousness has spurred efforts to develop methods to reclaim such byproducts and thereby minimize environmental impact. Additionally, the loss of this valuable catalytic material by disposal directly impacts the economics of the oligomerization process. Accordingly, a need has existed for recovering $BF_3$ values from oligomer reaction systems or mixtures. The invention addresses this need.

SUMMARY OF THE INVENTION

In one embodiment, therefore, the invention relates to a process in which a crude polyolefin-containing oligomerization reaction product liquid or liquid mixture containing dissolved $BF_3$ is recovered, and the dissolved $BF_3$ in the crude liquid mixture is vaporized therefrom in a vaporization zone. As used herein, the term "crude oligomerization reaction product mixture" is understood to refer to a liquid polyolefin-containing product mixture derived or obtained from a reaction zone or zones wherein an olefin is oligomerized in the presence of $BF_3$, as described more fully hereinafter. Additionally, the term "dissolved $BF_3$" is understood to refer not only to $BF_3$ that is dissolved in the reaction mixture but to include that $BF_3$ which may be loosely chemically held in the mixture. In this regard, evidence exists that $BF_3$ exists in the reaction mixture in different degrees of association. While not wishing to be bound by any theory of invention, it appears that $BF_3$ forms, on an equimolar basis, a strongly bonded complex with components of various promoter materials, e.g., the oxygen in oxygen-containing materials. This complex is not readily removed by vaporization from the reaction mixture. Additional $BF_3$ in or added to the mixture appears to be dissolved therein or only lightly bonded to the promoter or component thereof, and is susceptible to the recovery procedure of the invention.

The vaporized $BF_3$ leaves or is removed from the vaporization zone and is contacted in an absorption zone with a specified liquid olefin composition under conditions suitable for absorbing $BF_3$ in the olefin composition. In general, the olefin composition is supplied at a temperature sufficiently low, or the temperature in the absorption zone is maintained sufficiently low, so that, in combination with the quantity of liquid olefin composition supplied, $BF_3$ from the vaporization zone dissolves in the olefin composition to form dissolved $BF_3$. Most desirably, the volume of olefin composition supplied and the temperature thereof or of the absorption zone are so controlled that all of the $BF_3$ supplied to the absorption zone, on a continuous basis, is absorbed in the liquid olefin composition. The mixture comprising olefin and dissolved $BF_3$ may then be forwarded or transferred to a reaction zone where, under appropriate conditions, oligomerization of the olefin is permitted or allowed to occur by addition of $BF_3$ and perhaps a promoter or co-catalyst. In a preferred embodiment, the invention relates to a process for the oligomerization of an olefin in the presence of $BF_3$ catalyst and promoter, the process being characterized by removal of crude reaction product mixture and treatment as described to recover dissolved $BF_3$.

BRIEF DESCRIPTION OF THE DRAWING

The drawing is a schematic illustration of the process flow type.

DETAIL DESCRIPTION OF THE INVENTION

Processes for the oligomerization of an olefin or olefins utilizing $BF_3$ and a promoter are well known, as exemplified in U.S. Pat. No. 4,981,578, U.S. Pat. No. 4,032,591, and U.S. Pat. No. 4,409,415. Accordingly, only sufficient description of the reaction procedure is provided as is necessary for an understanding of the invention. Olefins commonly oligomerized by such procedures include linear and branched $C_4$ to $C_{30}$ olefins, preferably $C_6$ to $C_{20}$, which may be alpha or internal olefins, and mixtures thereof. Alpha olefins, and mixtures thereof, are preferred, particularly those containing 8 through 12 carbon atoms. The most preferred is 1-decene, usually supplied as a 1-decene composition which may be the pure or substantially pure material or a mixture comprising a substantial portion, say at least fifty percent by weight of 1-decene, such as a 75 weight percent mixture of 1-decene and other olefins. For simplicity, as used hereinafter, the term "olefin composition" is understood to include an olefin, a mixture of olefins, or an olefin- or olefins- containing composition, of the types above-mentioned, encompassing the presence, even in major amounts, of non-interfering or at least substantially non-interfering species, e.g., alkanes, in the composition. The term "1-decene composition", in a similar vein, is taken to include compositions ranging from "pure" 1-decene to mixtures with other olefins, or mixtures thereof, and includes, as noted, the presence, even in major amounts, of non-interfering or at least substantially non-interfering species, in the composition. Again, unless otherwise indicated or inconsistent with the circumstances, all percentages of components of a mixture expressed herein are by weight, based on the total weight of the mixture.

In general, the oligomerization reaction is carried out by combining the olefin composition and $BF_3$, preferably with the $BF_3$-promoter complex, in a reaction zone under suitable reaction conditions. Variation of reaction conditions is known to affect the character of the reaction product obtained; an oligomer of desired composition and properties may be obtained, for example, by regulating the temperature of the reaction. In this regard, the reaction will be conducted at suitable temperatures, e.g., from about $-20°$ C. to about $90°$ C. with temperatures within the range of from about $20°$ C. to about $90°$ C. being preferred. Similarly, pressures in the reactor may be varied, but normally will range from about one atmosphere to about 10 atmospheres, with pressures of from about 1.5 atmospheres to about 5.0 atmospheres being preferred.

Any of the known promoters that form a complex with $BF_3$ may be used. For example, straight and branched alkanols of 1 through 20 carbon atoms, (such as methanol, ethanol, n-propanol, isobutanol, n-hexanol, 2-ethylhexanol, n-decanol, n-dodecanol, and the like), and mixtures thereof, may be used. Also, water, fatty acids, i.e., hydrocarbyl acids containing from 1 to 20 carbon atoms (such as valeric, caproic, and the like), and mixtures thereof, organic esters (such as butyl acetate, methyl valerate, ethyl octanoate, and the like) and mixtures thereof, ketones (e.g., methyl ethyl ketone, methyl isobutyl ketone, and the like) and mixtures thereof, ethers (e.g., dibutyl ether, tetrahydrofuran, dioxane, and the like) and mixtures thereof, alkoxylated alkanols (such as 2-methoxyethanol, 2-ethoxyethanol, and the like) and mixtures thereof, polyhydric alcohols (e.g., glycol, glycerol, and the like) and mixtures thereof, inorganic acids (e.g., phosphoric and the like) and mixtures of such acids, silica, zeolites, and the like. Preferred promoters are straight and branched chain alkanols containing from 1 through 8 carbons, with straight and branched chain alkanols containing from 2 through 5 carbons being most preferred. The promoter-complex and/or $BF_3$ is present in a catalytic amount, as understood by those skilled in the art.

As mentioned, dissolved $BF_3$ in the crude reaction product mixture removed from the oligomerization reaction zone is vaporized from the crude reaction product mixture. The vaporization may be accomplished by any suitable combination of temperature and pressure. The temperature utilized will be a temperature sufficient to vaporize dissolved $BF_3$ from the crude oligomerization reaction product mixture, but insufficient to decompose or dissociate $BF_3$. If a promoter or co-catalyst complex is present in the mixture, the vaporization temperature employed will be insufficient to dissociate or decompose the $BF_3$-promoter complex or co-catalyst complex. As used herein, the expressions "insufficient to decompose" and "insufficient to dissociate", in the context of the vaporization procedure of the invention and with respect to the $BF_3$-promoter complex, are understood to permit or allow minor or very minor decomposition or dissociation of the $BF_3$-promoter complex or co-catalyst, provided at least the bulk of the complex or co-catalyst remains undissociated or combined. Preferably, vaporization is accomplished by heating the liquid oligomerization reaction product mixture to a suitable temperature and allowing the $BF_3$ to flash therefrom at atmospheric or reduced pressure. In general, temperatures of from about $10°$ C. to about $80°$ C. will release the $BF_3$ at atmospheric or below atmospheric pressure, with temperatures within the range of from about $20°$ C. to about $80°$ C. being preferred at the pressures mentioned. The relatively low temperatures for vaporization have the great advantage of minimizing undesirable effects on the oligomer in the crude reaction product mixture. Additionally, as a practical matter, since the $BF_3$ is to be reabsorbed or captured, lower temperatures in the range are desirable. The vaporization may be carried out in a zone or vessel which is "dedicated" to a specific oligomerization reactor or reaction zone, or, if multiple reactors or reaction zones are employed, a common vaporization vessel or zone may be used to vaporize the $BF_3$ from reaction mixture from multiple reaction zones.

Upon vaporization, the $BF_3$ passes or is forwarded to an absorption or contacting zone where it is contacted with a liquid olefin composition of the types mentioned. Single or multiple absorption or contacting vessels may be employed to receive the vaporized $BF_3$ from one or more vaporization vessels or zones, or the absorption "zone" may comprise one or more vessels with blending and/or concurrent introduction of the $BF_3$. The type of vessel or vessels employed in the contacting is not critical; the contacting may be carried out, e.g., in a countercurrent spray contactor or contactors, tray tower(s), or packed column(s). Accordingly, in the absorption zone, $BF_3$ is absorbed or dissolved under suitable conditions of temperature and pressure into the liquid olefin composition. Preferably, the volumes or flow of the olefin composition are controlled or regulated, as indicated, so that all the $BF_3$ forwarded from the vaporization zone will be absorbed or dissolved in the olefin composition.

The temperatures in the absorber should be maintained or regulated at levels that allow effective absorption of all $BF_3$ fed thereto; this may be accomplished preferably by chilling the olefin composition before entry into the absorption zone and/or by providing effective cooling in the absorption zone. Preferably, the temperature of liquid olefin composition on entry will be below about $40°$ C. most preferably $30°$ C. and the temperature in the absorber should not be allowed to exceed these values. Generally, the temperature will range from $-20°$ C. to $40°$ C. preferably $10°$ C. to $30°$ C.

In order to describe the invention more fully, the following illustration is made utilizing the accompanying drawing. In this illustration, all values given are calculated or merely exemplary, and the procedure is assumed to be continuous. As shown, an olefin-containing stream, e.g., a stream which may be 1-decene (75 percent 1-decene monomer, 25 percent other olefins and inert material), which further contains 0.14 percent propanol in line 1 enters reactor 2 where it is contacted with $BF_3$ supplied via line 3. Reactor 2, although illustrated as a single vessel, is preferably a series of vessels with feeds of $BF_3$ to each vessel, reacting liquid passing from one vessel to the next in the series, with crude oligomerization reaction product mixture being removed from the last vessel. The contacting is carried out under conditions to oligomerize the olefin, accompanied by intimate mixing of the reactants, total contact time being, for example, about two hours and ten minutes. A crude polydecene oligomerization reaction product mixture containing dissolved $BF_3$ is removed from the bottom of reactor 2 and forwarded via line 4 to a flash or vaporization zone 5. Flash zone 5 comprises a simple tank where the $BF_3$ is flashed from the crude reaction mixture by suitable temperature-pressure conditions. For example, prior to entry into zone or vessel 5, the crude oligomerization reaction product mixture may be heated to a temperature of $70°$ C. so that upon entry into tank 5, which is operated a slightly below atmospheric pressure, the $BF_3$ in the mixture flashes from the crude oligomerization reaction product mixture and passes overhead through line 6. The remaining crude oligomerization reaction product mixture, containing $BF_3$-complex, is removed from flash zone 5 via line 7 to further treatment and recovery of the contents thereof. $BF_3$ in line 6 is forwarded to absorption zone 8 where it is contacted intimately with a liquid olefin stream from line 9 comprising 1-decene (75 percent 1 decene monomer, 25 percent other olefins and inert material). Vessel 8 preferably comprises a packed tower wherein the $BF_3$ is passed countercurrent to the liquid olefin, inert material entering with the $BF_3$ passing overhead via line 10 to vent scrubber 11. The liquid olefin stream in line 9 is preferably at or cooled to a temperature of about 10° C. to assist in the absorption of $BF_3$; alternately or additionally the vessel may be cooled by suitable heat exchange means to ensure that effective dissolution of the $BF_3$ occurs while possible oligomerization of the olefin in the absorber is minimized. Accordingly, there is formed in absorber 8 a liquid olefin mixture containing, for example, 0.16 percent dissolved $BF_3$. This mixture, containing the vaporized $BF_3$ values from vessel 5, is admirably suited for oligomerization, and is forwarded via line 12 to reactor 13 wherein additional $BF_3$ and promoter, such as propanol, are added to raise the concentration of $BF_3$ and increase the ratio of $BF_3$ above 1 to 1 with respect to the propanol. Reactor 13 is maintained at appropriate reaction conditions, such as about 100° F. and 44 psig. Alternately (dotted line), the mixture in 12 may be returned to reaction zone 2 for reaction therein, or to some other site for utilization. Although not illustrated, the crude reaction mixture from 13 may be treated in a similar fashion to that from reactor 2, to the end that economic utilization of $BF_3$ is obtained.

The advantage of close temperature control of the absorbing liquid olefin composition, i.e., either providing a cooled liquid olefin composition or ensuring effective cooling in the absorber, is supported by the following experiments.

EXAMPLE I

Dry 1-decene was added to an autoclave, and $BF_3$ was added under minimal pressure (4 inches of water) until saturation was achieved, the temperature of the 1-decene being held at 30 ° C. The concentration of $BF_3$ absorbed at this temperature was determined by quantitative technique involving the hydrolysis of the saturated mixture and aqueous phase metals analysis for boron content by an inductively coupled plasma analytical instrument. The analysis showed the saturation concentration of $BF_3$ at 30° C. to be 0.19 wt. percent.

EXAMPLE II

The procedure of Example I was repeated, except that the temperature was maintained at 10° C. Analysis showed the saturation concentration of $BF_3$ at 10° C. to be 0.28 wt. percent, an increase of over 47 percent by weight.

While the invention has been illustrated with partic-ular apparatus, those skilled in the art will appreciate that, except where specified or otherwise required, other equivalent or analogous units may be employed. As indicated, the terms "zone" or "zones", as employed in the specification and claims, include, where suitable, the use of segmented equipment operated in series, or the division of one unit into multiple units because of size constraints, etc. For example, an absorption column might comprise two separate columns or vessels in which the liquid from the lower portion of the first column would be introduced into the upper portion of the second column, the gaseous material from the upper portion of the first column being fed to the lower portion of the second column.

What is claimed is:

1. A process for the oligomerization of an olefin composition and recovery of $BF_3$, comprising contacting an olefin composition in a reaction zone with $BF_3$ and in the presence of a $BF_3$-promoter complex, under conditions to oligomerize said olefin, forming a crude polyolefin oligomerization reaction product mixture containing dissolved $BF_3$ and $BF_3$-promoter complex;

recovering crude oligomerization reaction product mixture containing dissolved $BF_3$ and $BF_3$-promoter complex;

vaporizing $BF_3$ from said crude oligomerization reaction product mixture in a vaporization zone at a temperature insufficient to decompose $BF_3$ or $BF_3$ promoter complex in said mixture;

contacting $BF_3$ from said vaporization zone with a liquid olefin composition in an absorption zone under conditions to absorb $BF_3$ in said liquid olefin composition with minimal oligomerization of the olefin composition in the absorption zone, forming a mixture comprising liquid olefin composition and $BF_3$.

2. The process of claim 1 wherein the olefin composition oligomerized is selected from linear and branched olefins containing from 4 to 20 carbon atoms.

3. The process of claim 1 in which the $BF_3$-promoter complex is the reaction product of $BF_3$ and a composition selected from straight and branched alkanols of 1 through 20 carbon atoms, and mixtures thereof, water, hydrocarbyl acids containing from 1 to 20 carbon atoms, and mixtures thereof, organic esters, and mixtures thereof, ketones, and mixtures thereof, ethers, and mixtures thereof, alkoxylated alkanols, and mixtures thereof, polyhydric alcohols, and mixtures thereof, inorganic acids, and mixtures thereof, silica, zeolites, and mixtures thereof; and mixtures thereof.

4. A process for the oligomerization of a 1-decene composition and recovery of $BF_3$ comprising contacting 1-decene composition in a reaction zone with $BF_3$ and in the presence of a $BF_3$- promoter complex under conditions to oligomerize 1-decene, forming a crude polydecene reaction product mixture containing dissolved $BF_3$ and $BF_3$- promoter complex;

vaporizing $BF_3$ from said crude polydecene oligomerization reaction product mixture in a vaporization zone at a temperature insufficient to decompose $BF_3$, or $BF_3$ promoter complex in said mixture;

contacting $BF_3$ from said vaporization zone with a liquid 1-decene composition in an absorption zone under conditions to absorb $BF_3$ in said liquid 1-decene composition with minimal oligomerization of the 1-decene composition in the absorption zone, forming a mixture comprising liquid 1-decene composition and $BF_3$.

5. The process of claim 4 in which the $BF_3$-promoter complex is the reaction product of $BF_3$ and a composition selected from straight and branched alkanols of 1 through 20 carbon atoms, and mixtures thereof, water, hydrocarbyl acids containing from 1 to 20 carbon atoms, and mixtures thereof, organic esters, and mixtures thereof, ketones, and mixtures thereof, ethers, and mixtures thereof, alkoxylated alkanols, and mixtures thereof, polyhydric alcohols, and mixtures thereof, inorganic acids, and mixtures thereof, silica, zeolites, and mixtures thereof; and mixtures thereof.

* * * * *